United States Patent [19]  [11] 4,008,187
Turley  [45] Feb. 15, 1977

[54] POLYURETHANE FOAMS HAVING REDUCED FLAMMABILITY

[75] Inventor: Richard J. Turley, Orange, Conn.

[73] Assignee: Olin Corporation, New Haven, Conn.

[22] Filed: Jan. 29, 1975

[21] Appl. No.: 545,080

Related U.S. Application Data

[63] Continuation-in-part of Ser. No. 334,336, Feb. 21, 1973, Pat. No. 3,883,620.

[52] U.S. Cl. .............................................. 260/2.5 AJ
[51] Int. Cl.$^2$ ........................................ C08G 18/14
[58] Field of Search ...................... 260/2.5 AJ, 963

[56] References Cited

UNITED STATES PATENTS

| 3,179,629 | 4/1965 | Friedman | 260/2.5 AJ |
| 3,707,586 | 12/1972 | Turley | 260/2.5 AJ |
| 3,847,844 | 11/1974 | Fuzesi | 260/2.5 AJ |
| 3,883,620 | 5/1975 | Turley | 260/2.5 AJ |

*Primary Examiner*—C. Warren Ivy
*Attorney, Agent, or Firm*—James B. Haglind; Donald F. Clements; Thomas P. O'Day

[57] ABSTRACT

Polyurethane foams are prepared from compositions containing, as flame retardant additives, a select group of polyhaloalkyl phosphate esters.

19 Claims, No Drawings

POLYURETHANE FOAMS HAVING REDUCED FLAMMABILITY

This application is a continuation-in-part of U.S. Application Ser. No. 334,336, filed Feb. 21, 1973, now U.S. Pat. No. 3,883,620, issued May 13, 1975.

This invention relates to the preparation of polyurethane foam from compositions containing tetrahaloalkyl phosphate esters as flame-retardant additives.

The wide range of utility of polyurethane foam has been somewhat circumscribed by its flammability. Consequently, numerous efforts have been made in recent years to develop ways of imparting flame-retardancy to the foam. Such efforts have produced a variety of fire suppressant or flame-retardant compounds which are either incorporated in the polyurethane prepolymer mix or applied to the polyurethane after foaming.

However, many of the flame retardant additives developed in the art have been found unsatisfactory because they have a detrimental effect on the foam or considerably alter the basic properties of the foam. Furthermore, some of the prior art flame retardants are relatively costly to prepare and therefore they are not economically feasible to use in the manufacture of foam.

A variety of haloalkyl phosphate esters have been known in the art. See for example U.S. Pat. Nos. 3,027,296, and 3,318,978, the latter disclosing certain tetrachlorobutyl phosphate esters which are said to be useful as flame-retardants for acrylonitrile polymer compositions.

It is the primary object of this invention to provide polyurethane foam incorporating a select group of tetrahalobutyl phosphate esters, which are relatively easy to prepare and economically feasible, to use as flame-retardant additives in polyurethane foam.

The flame retardant additives of the present invention are tetrahalobutyl phosphates having the formula:

$$(Y_3CCH_2\underset{X}{C}HCH_2O)_nP(OR)_m \overset{O}{\|} \quad \text{I}$$

or the formula:

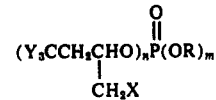

wherein
R represents an alkyl group having 1 to 4 carbon atoms,
X represents chlorine or bromine,
each Y represents independently chlorine or bromine,
n represents an integer from 1 to 3, and
m represents an integer from 0 to 2,
with the proviso that $m + n = 3$.

When incorporated in a polyurethane foam forming reaction mixture before foaming, these esters impart flame-retardant properties to the resulting foam.

It is to be understood that the term "flame retardant," as used in the specification and claim herein to describe the polyurethane foam of the invention is not intended to indicate that this foam in non-burning or fire-proof. Rather, the term refers to a reduction in the combustion rate of the foam under certain test conditions. Otherwise, when subjected to actual fire conditions, the foam will burn.

The esters can be prepared by various procedures such as described, for example, in Kosolapoff, G.M. Organophosphorus Compounds, 1950, pages 211, 213, 216, 224, 226 and 230. For example, esters of formulas I and II in which n is 3 can be prepared by reacting three moles of the appropriate tetrahalobutyl alcohol with one mole of phosphorus oxyhalide in the presence of an amine such as pyridine. This reaction is illustrated in equation III below.

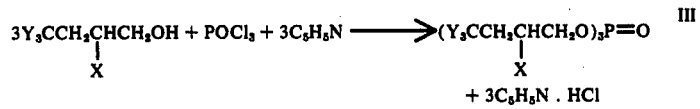

wherein X and Y have the significance indicated above.

Tetrahalobutyl esters of formulas I or II in which n is 2 can be prepared by reacting two moles of the appropriate tetrahalobutyl alcohol with one mole of phosphorus oxyhalide. The diester formed is further reacted with an aliphatic alcohol having 1 to 4 carbon atoms, both reactions taking place in the presence of an amine such as pyridine. These reactions are illustrated in equations IV and V below.

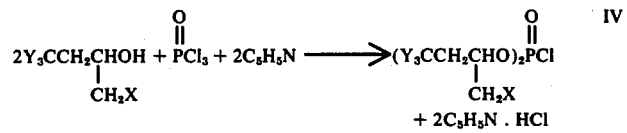

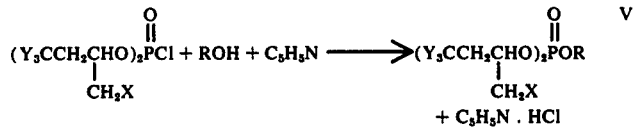

wherein X, Y and R have the significance indicated above.

Esters of formulas I or II in which n is 1 are prepared by reacting one mole of the appropriate tetrahalobutyl ester with one mole of phosphorus oxyhalide. The monoester thus formed is then further reacted with two moles of an aliphatic alcohol having 1 to 4 carbon atoms, both reactions taking place in the presence of an amine such as pyridine, as illustrated in equations VI and VII below.

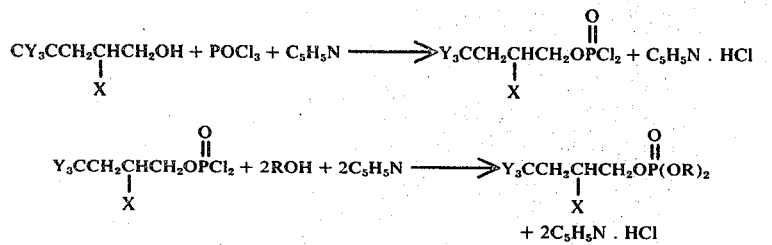

wherein X, Y and R have the significance indicated above.

An alternative method of preparation, particularly suitable for secondary alcohol derivatives, is the reaction of polyhaloalklyene oxide with phosphorus oxyhalide or phosphorus thiohalide in the presence of titanium tetrachloride.

Tetrahalobutyl alcohols used as starting materials in the preparation of the tetrahalobutyl phosphate esters may be prepared, for example, by the methods disclosed in U.S. Pat. No. 3,399,241, issued to E. Smith or U.S. Pat. No. 3,316,291, issued to Rostyslaw.

Illustrative examples of the compounds represented by formula I include:
Dimethyl 2,4,4,4tetrachlorobutyl phosphate
Tris(2,4,4,4-tetrachlorobutyl) phosphate
Propyl bis(2,4,4,4-tetrabromobutyl) phosphate
Dibutyl 2-chloro-4,4,4-tribromobutyl phosphate
Tris(2-bromo-4,4,4-trichlorobutyl) phosphate
Methyl bis(2-bromo-4,4,4-trichlorobutyl) phosphate
Diethyl 2-bromo-4,4,4-trichlorobutyl phosphate.

Illustrative examples of the compounds represented by formula II include:
Dimethyl 1,4,4,4-tetrachloro-2-butyl phosphate
Diethyl 1-bromo-4,4,4-trichloro-2-butyl phosphate
Methyl bis(1,4,4,4-tetrachloro-2-butyl) phosphate
Dipropyl 1-chloro-4,4,4-tribromo-2-butyl phosphate
Tris(1-bromo-4,4,4-trichloro-2-butyl) phosphate
Dimethyl 1-bromo-4,4,4-trichloro-2butyl phosphate
Dibutyl 1,4,4,4-tetrabromo-2-butyl phosphate
Tris(1,4,4,4-tetrachloro-2-butyl) phosphate.

Although the invention encompasses any phosphate ester of formulas I and II, preferred are those esters in which each Y represents chlorine, and of these, particularly preferred are those esters in which R represents ethyl or methyl.

Illustrative examples of the preferred esters according to the invention include:
Dimethyl 2,4,4,4-tetrachlorobutyl phosphate
Tris(2,4,4,4-tetrachlorobutyl) phosphate
Tris(2-bromo-4,4,4-trichlorobutyl) phosphate
Methyl bis(2-bromo-4,4,4-trichlorobutyl) phosphate
Diethyl 2-bromo-4,4,4-trichlorobutyl phosphate
Dimethyl 1,4,4,4-tetrachloro-2-butyl phophate
Diethyl 1-bromo-4,4,4-trichloro-2-butyl phosphate
Methyl bis(1,4,4,4-tetrachloro-2-butyl) phosphate
Tris(1-bromo-4,4,4-trichloro-2-butyl) phosphate
Dimethyl 1-bromo-4,4,4-trichloro-2-butyl phosphate
Tris(1,4,4,4-tetrachloro-2-butyl) phosphate.

The new compositions of the present invention are highly useful as flame retardant additives in the production of synthetic polymer compositions, such as urethane elastomers and foam. They are of particular utility in the production of flame retardant, flexible polyurethane foam.

In preparing flame-retardant polyurethane foam in accordance with the invention, either the so-called "one-shot method" or the "semi-prepolymer technique" ("quasi-prepolymer" technique) may be employed. Any combination of polyol components including polyester polyols or polyether polyols, organic polyisocyanate, foaming agent, catalyst, and other reactants capable of forming a cellular urethane material can be used. For example, it is well known in the art, to prepare flexible polyurethane foam-forming formulations comprising a polyether polyol component having a hydroxyl number of less than about 250, an organic polyisocyanate, a foaming agent, and a catalyst. Typical formulations are described in U.S. Pat. No. 3,072,582, issued Jan. 8, 1963, and No. 3,437,804, issued Oct. 17, 1967, and in Canadian Pat. No. 705,938, issued Mar. 16, 1965.

While, as indicated above, both polyether and polyester polyols can be employed in the practice of this invention, preferred embodiments utilize polyether polyols in the preparation of the polyurethane foam forming reaction mixture. Any suitable polyether polyol may be used for this purpose. These polyether polyols usually have a hydroxyl number for example from about 25 to about 800.

The polyether polyols include for example oxyalkylated polyhydric alcohols having a molecular weight range of about 200–10,000 and preferably between about 250–8,000. These oxyalkylated polyhydric alcohols are generally prepared by methods well known in the art such as reacting, in the presence of an alkaline catalyst, a polyhydric alcohol and an alkylene oxide such as ethylene oxide, propylene oxide, butylene oxide, amylene oxide, epichlorohydrin, and mixtures of these alkylene oxides, using either random or step-wise addition.

Polydhydric alcohols suitable for use in preparing the polyether polyols include ethylene glycol, pentaerythritol, methyl glucoside, propylene glycol, 2,3-butylene glycol, 1,3-butylene glycol, 1,5-pentane diol, 1,6-hexane diol, glycerol, trimethylolpropane, sorbitol, sucrose, dextrose, mixtures thereof the like. If desired, a portion or all of the polyhvdric alcohol may be replaced with another compound having at least two reactive hydrogen atoms, such as alkyl amines, alkylene polyamines, cyclic amines, amides, and polycarboxylic acids. Suitable alkyl amines and alkylene polyamines include methylamine, ethylamine, propylamine, butylamine, hexylamine, ethylenediamine, 1,6-hexanediamine, diethylenetriamine, and the like. Also, such cyclic amines as piperazine, 2-methylpiperazine and 2,5-dimethylpiperazine can also be used. Amides, such as acetamide, succinamide and benzenesulfonamide, constitute a further class of such reactive hydrogen compounds. A still further class of such reactive hydrogen compounds is the di- and polycarboxylic acids, such as adipic acid, succinic acid, glutaric acid, aconitic acid, diglycollic acid, and the like. It will be recognized that the reactive hydrogen compound can be one containing different functional groups having reactive hydrogen atoms, such a citric acid, glycollic acid, ethanolamine, and the like. Aromatic polyamines such as toluene diamine may also be employed. Mixture of oxyalkylated polyhydric alcohols are also suitable for use in the process of this invention.

Although as indicated above, the polyurethane foams of the invention can be flexible, semi-rigid, or rigid, the flexible foams are preferred. Therefore in preparing the polyurethane foam in accordance with this preferred embodiment of the invention, oxyalkylated polyhydric alcohol is used having a molecular weight of about 2000–7000 and more preferably about 2500–6000.

The organic polyisocyanates used in the preparation of the polyurethane foams include toluene diisocyanate, such as the 80:20 mixture or the 65:35 mixture of the 2,4- and 2,6-isomers, ethylene diisocyanate, propylene diisocyanate, methylene-bis-4-phenyl isocyanate, 3,3'-bitoluene-4,4'-diisocyanate, hexamethylene diisocyanate, napthalene1,5-diisocyanate, polyphenylene polymethylene isocyanate, mixtures thereof and the like. The preferred organic polyisocyanate is toluene diisocyanate. The amount of isocyanate employed in the process of this invention should be sufficient to provide at least about 0.7 NCO group per hydroxyl group present in the reaction system, which includes the polyol as well as any additive or foaming agent employed. An excess of isocyanate compound may be conveniently employed; however, this is generally undesirable due to the high cost of the isocyanate compounds. It is preferable, therefore, to employ sufficient isocyanate to provide no greater than about 1.25 NCO groups per hydroxyl group, and preferably between about 0.9 and about 1.15 NCO groups per hydroxyl group. The ratio of NCO to OH groups times 100 is referred to as the "index."

The polyurethane foams are prepared in the presence of a foaming agent which may be any of those known to be useful for this purpose. Illustrative are water and organic foaming agents containing up to about seven carbon atoms such as the halogenated hydrocarbons, lower molecular weight alkanes, alkenes, ethers, and mixtures thereof. Typical halogenated hydrocarbons include, but are not limited to: monofluorotrichloromethane, dichlorofluoromethane, difluorodichloromethane, 1,1,2-trichloro-1,2,2-trifluoroethane, dichlorotetrafluoroethane, ethyl chloride, methylene chloride, chloroform, and carbon tetrachloride. Other useful foaming agents include lower molecular weight alkanes, alkenes and ethers such as methane, ethane, ethylene, propane, propylene, pentane, hexane, heptane, ethyl ether, diisopropyl ether, mixtures thereof, and the like. The amount of foaming agent employed may be varied within a wide range. Generally, however, the halogenated hydrocarbons are employed in an amount from about 1 to about 50, and preferably about 5–35, parts per 100 parts by weight of the polyol, and generally water is employed in an amount from about 1.0 to 6.0 parts by weight per 100 parts by weight of the polyol.

The polyurethane foams are prepared in the presence of a catalytic amount of a reaction catalyst. The catalyst employed may be any of the catalysts known to be useful for this purpose, such as tertiary amines and metallic salts, particularly stannous salts, and mixtures thereof. Typical tertiary amines include, but are not limited to, the following: 1,4-diazabicyclo [2,2,2] octane, i.e., triethylene diamine, N-hydroxyethyl morpholine, triethylamine and trimethylamine. Typical metallic salts include, for example, the salts of antimony, tin and iron, e.g., dibutyltin dilaurate, stannous octoate, and the like. Any catalytic proportion of catalyst or catalyst mixture may be employed such as between about 0.1 and about 3.0 percent, and preferably between about 0.5 and about 2.5 percent, by weight of the polyol.

It is preferred in the preparation of the polyurethane foams of the present invention to employ minor amounts of a conventional surfactant in order to further improve the cell structure of the polyurethane foam. Typical of block copolymers. U.S. Pat. No. 2,834,748 and T. H. Ferrigno, *Rigid Plastic Foams* (New York: Reinhold Publishing Corp., 1963) pages 38–42, disclose various surfactants which are useful for this purpose. Generally up to 2 parts by weight of the surfactant are employed per 100 parts of the polyol.

In utilizing the tetrahalobutyl phosphate esters as flame-retardants for polyurethane foam, they are added to the polyurethane foam-forming reaction mixture prior to foaming. Conveniently, they are first blended with the polyol component used in making the foam, and the blend is then added to the other ingredients of the polyurethane foam-forming reaction.

The tetrahalobutyl phosphate esters of the present invention can be used in any proportion which is effective in imparting flame-retardant properties to the foam without adversely affecting or altering the properties of the foam. Usually an additive proportion is used, for example, from about 5 to about 30 parts per 100 parts by weight of the polyol component used in making the foam. Preferably, 10–25 parts per 100 parts by weight of the polyol component are used. However, greater or lesser amounts may be used if desired.

The following examples are presented to further illustrate the invention without any intention of being limited thereby. All parts and percentages are by weight unless otherwise specified.

EXAMPLE I (Dimethyl 2,4,4,4-tetrachlorobutyl phosphate)

Into a 3-necked flask fitted with a stirrer, thermometer and drying tube, a solution of 91.8 g. (0.6 mole) $POCl_3$ and 127 g. (0.6 mole) 2,4,4,4-tetrachlorobutanol in a mixture of 400 mls. of carbon tetrachloride and 100 mls. of chloroform was poured. A total of 52 g. (0.67 mole) of pyridine was added dropwise while stirring and holding the temperature below 12° C. A mixture of 42 g. (1.3 moles) of methanol in 104 g. (1.3 moles) of pyridine was added while keeping the temperature below 21° C. After completion of the reaction the organic phase was successively washed with aqueous 20% $H_2SO_4$ solution, water, saturated aqueous $NaHCO_3$, and water. The solution was dried and concentrated at reduced pressure to give 158 g. (82%) of dimethyl-2,4,4,4-tetrachlorobutyl phosphate. Distillation at 130° C./0.3 mm. gave a purified product having n(24/D) 1.4766. The phosphate structure was substantiated by infrared analysis. Elemental Analysis: Calcd. for $C_6H_{11}Cl_4O_4P$: percent Cl, 44.38; percent P, 9.69 Found: percent Cl, 45.49; percent P, 9.48.

EXAMPLE II

Tris(2,4,4,4-tetrachlorobutyl) phosphate

A total of 46.1 g. (0.3 mole) of phosphorus oxychloride was added dropwise to 191 g. (0.9 mole) of stirred 2,4,4,4-tetrachlorobutanol at 80° –85° C. The mixture was held at 80° –90° C. under reduced pressure until HCl evolution ceased. The mixture was then dissolved in $CCl_4$, and successively washed with $H_2O$, saturated aqueous $NaHCO_3$, and water. The solvent was removed under reduced pressure, the product dissolved in dioxane, and treated with an acetic anhydridepyridine mixture. The mixture was washed and the solvent removed by heating in vacuo to give 87 g. (43%) of tris(2,4,4,4-tetrachlorobutyl) phosphate, n(26/D) 1.5212. Infrared analysis confirmed the phosphate structure. Elemental Analysis: Calcd. for $C_{12}H_{15}Cl_{12}O_4P$: percent Cl, 62.65; percent P, 4.56 Found: percent Cl, 63.67; percent P, 4.40.

EXAMPLE III (Dimethyl 1,4,4,4-tetrachloro-2-butyl phosphate)

Pyridine, 85 g. (1.07 moles), was added dropwise at 15° –20° C. to a solution of 212 g. (1.0 mole) 1,4,4,4-tetrachloro-2-butanol and 153 g. (1.0 mole) phosphorus oxychloride in 500 ml. of a carbon tetrachloride-chloroform mixture (4:1 by volume) with vigorous stirring. A solution of 67.3 g. (2.1 moles) methanol in 168 g. (2.1 moles) pyridine was then added dropwise at 25° –27° C. The product was washed as in Example II and treated with an acetic anhydridepyridine mixture. A total of 99.6 g. (30%) of dimethyl 1,4,4,4-tetrachloro-2-butyl phosphate was distilled at 129° –31° C./0.25 mm.; n(23/D) 1.4785. The phosphate structure was confirmed by infrared analysis. Elemental Analysis: Calcd. for $C_6H_{11}Cl_4O_4P$: percent Cl, 44.38; percent P, 9.69 Found: percent Cl, 44.33; percent P, 9.26.

EXAMPLE IV (Dimethyl 1-bromo-4,4,4-trichloro-2-butyl phosphate)

To a vigorously stirred solution of 154 g. (0.6 mole) of 1-bromo-4,4,4-trichloro-2-butanol and 92 g. (0.6 mole) phosphorous oxychloride in 100 ml. of a mixture of $CCl_4$-$CHCl_3$ (4:1 by volume) was added dropwise 53 g. (0.68 mole pyridine at about 23° C. Following completion of the reaction, the mixture was heated to 52° C. After cooling to 23° –28° C., a mixture of 41.5 g. (1.3 mole) methanol in 106 g. (1.3) pyridine was added dropwise. The product was worked up as in Example III and solvent was removed in vacuo to give 181 g.(83%) of dimethyl 1-bromo-4,4,4-trichloro-2-butyl phosphate as a light yellow liquid, n(25/D) 1.4968. Infrared analysis confirmed the phosphate structure. Elemental Analysis: Calcd. for $C_6H_{11}BrCl_3O_4P$: percent Br, 21.92; percent Cl, 29.18 percent P, 8.49. Found: percent Br, 22.38; percent Cl, 30.13; percent P, 8.05.

EXAMPLE V

Methyl bis(1,4,4,4-tetrachloro-2-butyl) phosphate

Dropwise addition of 123 g. (1.55 mole) pyridine to a well-stirred solution of 318 g. (1.5 mole) 1,4,4,4-tetrachloro-2-butanol and 76.5 g. (0.5 mole) phosphorus oxychoride in 200 ml. $CCl_4$ was made while the temperature kept below 15° C. Upon completion of the reaction, the mixture was heated to 53° C., cooled to room temperature and 70 ml. methanol added. The product was worked up as in Example IV and unreacted alcohol was removed by distillation. A total of 215 g. (86%) of methyl bis(1,4,4,4tetrachloro-2-butyl) phosphate was obtained as a light brown viscous oil, n(24/D) 1.5102. Infrared analysis confirmed the phosphate structure. Elemental Analysis: Calcd. for $C_9H_{13}Cl_8O_4P$: percent Cl, 56,80; percent P, 6.20 Found: percent Cl, 56.66; percent P, 5.92.

EXAMPLE VI

Flame-retardant polyurethane foam

A flexible polyurethane foam-forming reaction mixture was prepared consisting of the following ingredients in the indicated proportions:

| Ingredients | Amount |
| --- | --- |
| Oxypropylated glycerin (mol. wt. 3,000) | 100.0 gms. |
| Flame-retardant additive | 20.0 gms. |
| Silicone surfactant DC-190* | 1.5 mls. |
| 1,4-Diazabicyclo[2.2.2]octane | 0.4 mls. |
| Water | 4.0 mls. |
| Stannous octoate catalyst | 0.6 mls. |
| Toluene diisocyanate (80/20 mixture of 2,4 and 2,6 isomers) | 41.0 mls. |

*Dow Corning 190. This surfactant is a block copolymer of polydimethylsiloxane and a polyester resin.

In a formulation, dimethyl 1,4,4,4-tetrachloro-2-butyl phosphate as flame retardant was blended at ambient temperature with the oxypropylated glycerine. The other ingredients were blended into the mixture and after a final brief blending the mixture was poured into an open-top form whereupon foaming of the reaction mixture occurred. The foam was oven cured at 95° C. for about 10 minutes and further cured at ambient temperature for about two days. The flammability of the foam was tested by the method described in ASTM D1692-68. An average extent of burn (AEB) of 1.4 inches was obtained according to that test. This indicates the extent of burning to be limited to an average of 1.4 inches using a standard foam sample 6 inches in length.

EXAMPLE VII

Flame-retardant polyurethane foam

Example VI was repeated using dimethyl 1-bromo-4,4,4-trichloro-2-butyl phosphate as the flame-retardant additive. An AEB of 1.7 inches was obtained.

EXAMPLE VIII

Flame-retardant polyurethane foam

Example VII was repeated using dimethyl 2,4,4,4-tetrachlorobutyl phosphate as the flame-retardant additive. An AEB of 2.0 inches was obtained.

What is claimed is:

1. A polyurethane foam prepared from a reaction mixture which comprises a flame retarding proportion of a tetrahalobutyl phosphate ester of the formula:

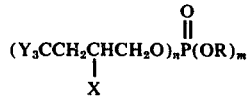

-continued or

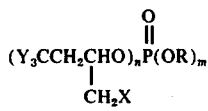

wherein
R represents an alkyl group having 1 to 4 carbon atoms,
X represents chlorine or bromine, each Y represents independently chlorine or bromine,
n represents an integer from 1 to 3, and
m represents an integer from 0 to 2,
with the proviso that m + n = 3.

2. A polyurethane foam of claim 1 wherein said reaction mixture comprises a polyether or polyester polyol, an organic polyisocyanate, a foaming agent, and a reaction catalyst.

3. The polyurethane foam of claim 2 wherein said tetrahalobutyl phosphate ester is represented by the formula:

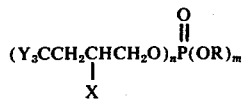

wherein R represents methyl or ethyl X represents chlorine or bromine
each Y represents independently chlorine or bromine
n represents an integer from 1 to 3, and m represents an integer from 0 to 2 with the proviso that m + n = 3.

4. The polyurethane foam of claim 3 wherein said Y is chlorine.

5. The polyurethane foam of claim 1 wherein said tetrahalobutyl phosphate ester is selected from the group consisting of
Dimethyl 2,4,4,4-tetrahclorobutyl phosphate,
Tris(2,4,4,4-tetrachlorobutyl) phosphate,
Propyl bis(2,4,4,4-tetrabromobutyl) phosphate,
Dibutyl 2-chloro-4,4,4-tribromobutyl phosphate,
Tris(2-bromo-4,4,4-trichlorobutyl) phosphate,
Methyl bis(2-bromo-4,4,4-trichlorobutyl) phosphate, and
Diethyl 2-bromo-4,4,4-trichlorobutyl phosphate.

6. The polyurethane foam of claim 5 wherein said tetrahalobutyl phosphate ester is dimethyl 2,4,4,4-tetrachlorobutyl phosphate.

7. The polyurethane foam of claim 2 wherein said tetrahalobutyl phosphate ester is represented by the formula:

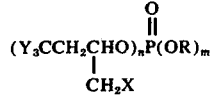

wherein
R represents an alkyl group having 1 to 4 carbon atoms

X represents chlorine or bromine
each Y represents independently chlorine or bromine
n represents an integer from 1 to 3, and
m represents an integer from 0 to 2
with the proviso that m + n = 3.

8. The polyurethane foam of claim 7 wherein said Y is chlorine.

9. The polyurethane foam of claim 7 wherein said tetrahalobutyl phosphate ester is selected from the group consisting of
Dimethyl 1,4,4,4-tetrachloro-2-butyl phosphate,
Diethyl 1-bromo-4,4,4-trichloro-2-butyl phosphate,
Methyl bis(1,4,4,4-tetrachloro-2-butyl) phosphate,
Dipropyl 1-chloro-4,4,4-tribromo-2-butyl phosphate,
Tris (1-bromo-4,4,4-trichloro-2-butyl) phosphate,
Dimethyl 1-bromo-4,4,4-trichloro-2-butyl phosphate,
Dibutyl 1,4,4,4-tetrabromo-2-butyl phosphate, and
Tris(1,4,4,4-tetrachloro-2-butyl) phosphate.

10. The polyurethane foam of claim 9 wherein said R is methyl or ethyl.

11. The polyurethane foam of claim 10 wherein said tetrahalobutyl phosphate ester is selected from the group consisting of dimethyl 1,4,4,4-tetrachloro-2-butyl phosphate and dimethyl 1-bromo-4,4,4-trichloro-2-butyl phosphate.

12. A flexible polyurethane foam of claim 5 wherein said polyether polyol is an oxyalkylated polyhydric alcohol having a molecular weight of about 2000 to about 7000.

13. The flexible polyurethane foam of claim 12 wherein said organic isocyanate is toluene diisocyanate.

14. The flexible polyurethane foam of claim 13 wherein said catalyst is a mixture of stannous octoate and 1,4-diazabicyclo [2,2,2] octane.

15. A flexible polyurethane foam of claim 9 wherein said polyether polyol is an oxyalkylated polyhydric alcohol having a molecular weight of about 2000 to about 7000.

16. The flexible polyurethane foam of claim 12 wherein said organic isocyanate is toluene diisocyanate.

17. The flexible polyurthane foam of claim 16 wherein said catalyst is a mixture of stannous octoate and 1,4-diazabicyclo [2,2,2] octane.

18. The polyurethane foam of claim 4 wherein said tetrahalobutyl phosphate ester is selected from the group consisting of
Dimethyl 2,4,4,4-tetrachlorobutyl phosphate,
Tris(2,4,4,4-tetrachlorobutyl) phosphate,
Tris(2-bromo-4,4,4-trichlorobutyl) phosphate,
Methyl bis(2-bromo-4,4,4-trichlorobutyl) phosphate, and
Diethyl 2-bromo-4,4,4-trichlorobutyl phosphate.

19. The polyurethane foam of claim 10 wherein said tetrahalobutyl phosphate ester is selected from the group consisting of
Dimethyl 1,4,4,4-tetrachloro-2-butyl phosphate,
Diethyl 1-bromo-4,4,4-trichloro-2-butyl phosphate,
Methyl bis(1,4,4,4-tetrachloro-2-butyl) phosphate,
Tris(1-bromo-4,4,4-trichloro-2-butyl) phosphate,
Dimethyl 1-bromo-4,4,4-trichloro-2-butyl phosphate, and
Tris(1,4,4,4-tetrachloro-2-butyl) phosphate.

* * * * *